(12) United States Patent
Nagel et al.

(10) Patent No.: US 8,465,459 B2
(45) Date of Patent: Jun. 18, 2013

(54) MEDICAMENT CONTAINER

(75) Inventors: Thomas Nagel, Tharandt (DE); René Richter, Tharandt (DE); Robert Witt, Dresden (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 13/389,866

(22) PCT Filed: Aug. 20, 2010

(86) PCT No.: PCT/EP2010/062153
§ 371 (c)(1),
(2), (4) Date: Jun. 6, 2012

(87) PCT Pub. No.: WO2011/023631
PCT Pub. Date: Mar. 3, 2011

(65) Prior Publication Data
US 2012/0253282 A1   Oct. 4, 2012

(30) Foreign Application Priority Data

Aug. 27, 2009 (EP) ..................... 09010969

(51) Int. Cl.
| A61M 5/178 | (2006.01) |
| A61M 5/30 | (2006.01) |
| A61M 31/00 | (2006.01) |
| A61M 37/00 | (2006.01) |
| A61M 5/32 | (2006.01) |
| A61F 7/12 | (2006.01) |

(52) U.S. Cl.
USPC .......... 604/185; 604/113; 604/71; 604/95.05; 604/163

(58) Field of Classification Search
USPC ......... 604/71, 89–91, 95.04–95.05, 184–186, 604/217, 412, 113, 21, 131–132, 891.1–892.1, 604/257–261, 408–410, 163
See application file for complete search history.

(56) References Cited

U.S. PATENT DOCUMENTS

| 4,192,308 | A | * | 3/1980 | Michaels | .................... 604/892.1 |
| 4,367,741 | A | * | 1/1983 | Michaels | .................... 604/892.1 |
| 4,455,144 | A | * | 6/1984 | Michaels | .................... 604/892.1 |
| 4,518,384 | A | | 5/1985 | Tarello et al. | |
| 4,857,055 | A | * | 8/1989 | Wang | ............................ 604/133 |

(Continued)

FOREIGN PATENT DOCUMENTS

| EP | 1362609 | 11/2003 |
| FR | 2884722 | 10/2006 |

(Continued)

OTHER PUBLICATIONS

International Preliminary Report on Patentability for International App. No. PCT/EP2010/062152, issued Feb. 28, 2012.

(Continued)

*Primary Examiner* — Manuel Mendez
*Assistant Examiner* — Rebecca E Eisenberg
(74) *Attorney, Agent, or Firm* — McDonnell Boehnen Hulbert & Berghoff LLP

(57) ABSTRACT

The invention relates to a medicament container for a liquid medicament, the medicament container comprising a bag with an outlet, the bag being compressible or shrinkable by subjection of at least a part of the medicament container to an energy source.

16 Claims, 2 Drawing Sheets

U.S. PATENT DOCUMENTS

| | | | |
|---|---|---|---|
| 5,080,652 A * | 1/1992 | Sancoff et al. | 604/132 |
| 5,263,935 A * | 11/1993 | Hessel | 604/132 |
| 5,284,481 A * | 2/1994 | Soika et al. | 604/132 |
| 5,394,907 A * | 3/1995 | Hjertman et al. | 141/1 |
| 5,474,527 A | 12/1995 | Bettinger | |
| 6,190,366 B1 * | 2/2001 | Tani | 604/279 |
| 6,413,239 B1 * | 7/2002 | Burns et al. | 604/132 |
| 8,038,650 B2 * | 10/2011 | Shekalim | 604/132 |
| 2002/0068137 A1 * | 6/2002 | Paleari et al. | 428/34.9 |
| 2002/0107472 A1 | 8/2002 | Thompson | |
| 2005/0187522 A1 | 8/2005 | Miller | |
| 2007/0036835 A1 * | 2/2007 | Coppeta et al. | 424/426 |
| 2008/0058755 A1 * | 3/2008 | Yee | 604/410 |
| 2008/0183135 A1 * | 7/2008 | Forrest | 604/132 |
| 2012/0197195 A1 * | 8/2012 | Basso et al. | 604/132 |

FOREIGN PATENT DOCUMENTS

| | | |
|---|---|---|
| WO | 03/045481 | 6/2003 |
| WO | 2008/153769 | 12/2008 |
| WO | 2009/069518 | 6/2009 |

OTHER PUBLICATIONS

International Search Report for International App. No. PCT/EP2010/062153, completed Feb. 21, 2011.

* cited by examiner

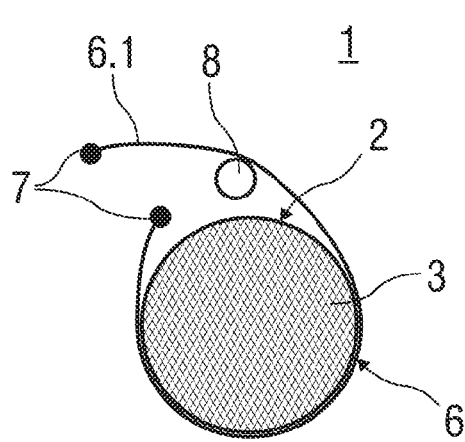
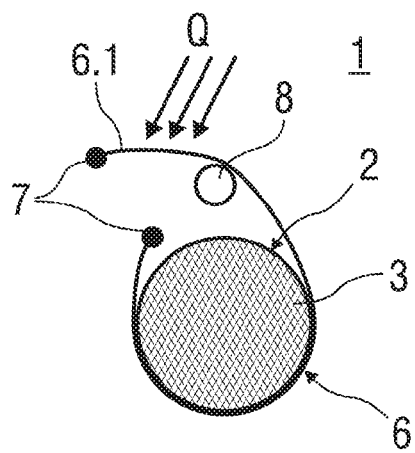
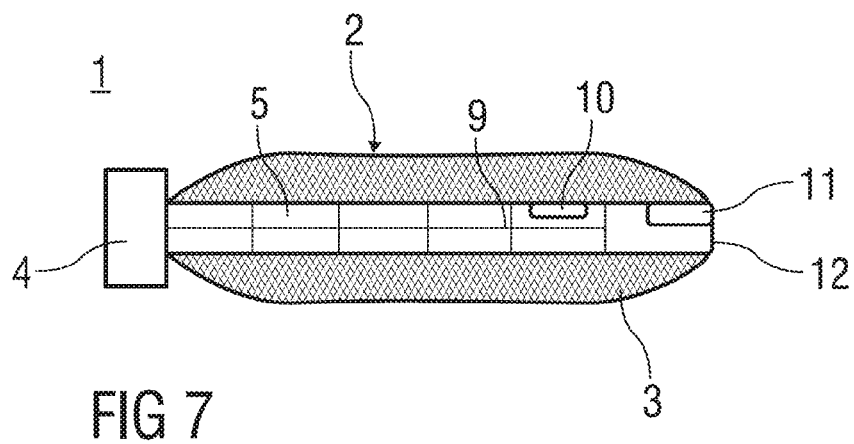
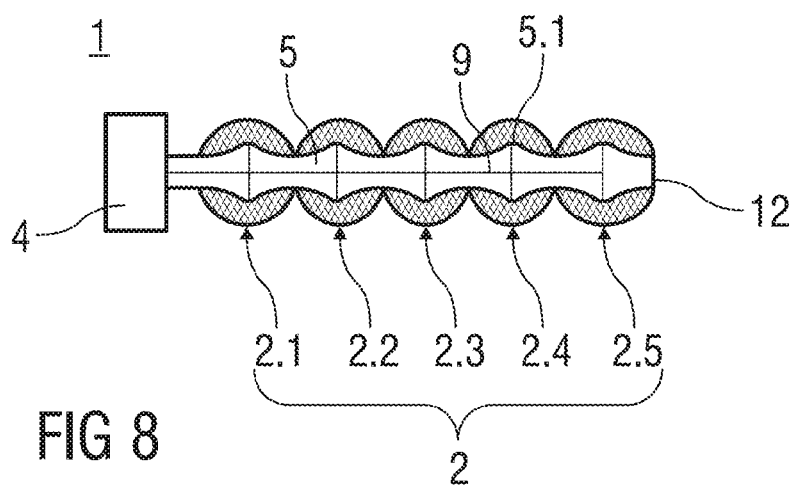

MEDICAMENT CONTAINER

CROSS REFERENCE TO RELATED APPLICATIONS

The present application is a U.S. National Phase Application pursuant to 35 U.S.C. §371 of International Application No. PCT/EP2010/062153 filed Aug. 20, 2010, which claims priority to European Patent Application No. 09010969.5 filed on Aug. 27, 2009. The entire disclosure contents of these applications are herewith incorporated by reference into the present application.

TECHNICAL FIELD

The invention relates to a medicament container for a liquid medicament, the medicament comprising a bag with an outlet.

BACKGROUND

Many medicaments have to be injected into the body. This applies in particular to medicaments, which are deactivated or have their efficiency remarkably decreased by oral administration, e.g. proteins (such as insulin, growth hormones, interferons), carbohydrates (e.g. heparin), antibodies and the majority of vaccines. Such medicaments are predominantly injected by means of syringes, medicament pens or medicament pumps.

Some medicaments have to be administered by inhaling them from so called inhalers.

WO 2009/069518 A1 discloses an inhaler, wherein the medicament to be inhaled is stored in a bag shaped medicament container.

U.S. Pat. No. 5,474,527 discloses a microprocessor controlled transdermal medication patch system wherein the medication is dispensed internally by positive displacement from multiple reservoirs within the patch so as to vary the drug selection, sequence, and concentration and thereby the regimen and release rate. In a preferred embodiment, electric resistance heating elements activate multiple heat-shrink polymer reservoirs to dispense beneficial fluids into a common absorbent layer for transdermal passage.

SUMMARY

It is an object of the present invention to provide an improved medicament container.

The object is achieved by a medicament container according to claim 1.

Preferred embodiments of the invention are given in the dependent claims.

A medicament container for a liquid medicament according to the invention comprises a bag with an outlet. The bag is compressible or shrinkable by subjection of at least a part of the medicament container to an energy source. The bag may be flexible. By compressing or shrinking the bag the liquid medicament stored inside is displaced and thereby delivered through the outlet. The inventive design allows for setting aside external displacing mechanisms like piston rods. Friction is avoided since no movable parts are required. Due to the small part count the medicament container may be easily produced. In order to avoid dead volume the bag has a rigid core arranged inside.

In a preferred embodiment of the invention the bag is compressible or shrinkable by subjection of at least a part of the medicament container to a heat source. This may be achieved by application of heat shrink materials which are known from heat shrink tubings or the like. Heat shrink materials are thermoplastic materials such as polyolefin, fluoropolymer (such as FEP, PTFE or Kynar), PVC, neoprene, silicone elastomer or Viton. The heat shrinking effect may be based on monomers contained in the material which polymerise when heated. Thus the density of the material is increased as the monomers become bonded together, therefore taking up less space. Consequently, the volume of the material shrinks.

Alternatively, heat shrinking may be expansion-based. In this case the material is produced, heated to just above the polymer's crystalline melting point, mechanically stretched and rapidly cooled while still stretched. When heated the material will return to a relaxed state and shrink. The mechanical stretching in the case of a tube or bag may be achieved by inflating with a gas.

In one embodiment of the invention the bag consists of a thermoplastic heat shrink material being configured to shrink when subjected to heat. This embodiment is particularly advantageous in terms of part count and costs.

In an alternative embodiment an actor made of the heat shrinking material is at least partially arranged around the bag. This embodiment as opposed to the aforementioned one avoids subjecting the medicament stored in the bag to heat which could otherwise affect the quality of the medicament.

The actor material may comprise a section arranged around the bag and a remote section, which is not in contact with the bag and which is arranged for being subjected to heat while the section arranged around the bag remains cold. Thus the contents of the bag are even more effectively kept from warming.

In a further embodiment, the actor material may comprise several sections which may be heated separately. Preferably, each section corresponds with a predetermined dose. Thus, a multi-injection device is easily provided.

Since the shrinking of the heat shrink material in either embodiment is limited there may remain a dead volume in the bag after subjection to heat. In order to avoid the dead volume the bag has a rigid core arranged inside. Preferably, an outline of the rigid core essentially equals an internal diameter of the bag after heating.

The bag may be designed in different manner that a single dose with the total capacity, a plurality of dose with predetermined dose rate or a plurality of dose with arbitrary dose rate may be delivered.

The outlet may comprise an interface for receiving a hollow injection needle. Alternatively, the needle may be integrated with the medicament container.

The medicament container may be part of an injection arrangement or an inhaler arrangement for delivering a liquid medicament to a human or an animal.

The injection arrangement may comprise a valve and a hollow needle for piercing a patient's skin, the valve and needle being arranged at the outlet of the medicament container. In case of a jet injector, instead of the needle, a jet nozzle may be arranged.

At least one drain channel may be arranged in the rigid core in a manner to connect at least one opening on a surface of the rigid core to the outlet. After application of energy or heat the bag shrinks and displaces virtually all of the liquid medicament. Non-uniform heating or subjection to energy may lead to non-uniform shrinking in such a manner that the shrunk bag seals against the rigid core near the outlet while residual medicament is still trapped in more remote areas. This problem is avoided by the drain channels in the rigid core allowing the bag to shrink until being flush with the rigid core so as to be reliably emptied irrespective of the uniformity of the shrinking process.

The bag may be subdivided into at least two consecutive bag chambers, wherein the rigid core comprises a respective segment for each bag chamber, wherein each segment exhibits at least one opening of the drain channel. The bag chambers may be interconnected for fluid communication. Alternatively, the bag chambers may be separate from each other. The separate bag chambers may contain the same or different medicaments. In the case of different medicaments the drain channel may comprise valves for keeping the different medicaments separate before application, wherein the valves are arranged to allow flow of medicament when the pressure of the medicament exceeds a predefined threshold when the bag chamber is shrunk. The bag chambers may have the same or different volumes. These volumes may be used for fixed doses and/or variable doses, i.e. the volumes of the chambers may be partially or entirely emptied.

Each segment may comprise a central bulge, in particular if the bag chambers have a spheroid outline. Thus, when the bag chamber is shrunk the it becomes essentially simultaneous flush with the rigid core so as to avoid cavities with residual fluid.

At least one sensor may be integrated in the rigid core. The sensor may serve for determining the state of the liquid medicament.

An energy store, such as a battery, may be arranged or integrated in the rigid core. The energy store may be arranged for powering the sensor and/or for providing the energy required to shrink the bag.

An end of the rigid core opposite the outlet may be arranged as an interface for exchanging data of the sensor and/or energy from the energy store between the medicament container and at least one external component.

The medicament container may preferably be used for delivering one of an analgetic, an anticoagulant, insulin, an insulin derivate, heparin, Lovenox, a vaccine, a growth hormone, a peptide hormone, a proteine, antibodies and complex carbohydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

The present invention will become more fully understood from the detailed description given herein below and the accompanying drawings which are given by way of illustration only, and thus, are not limitive of the present invention, and wherein:

FIG. 5 is a schematic cross section of an embodiment of a medicament container with a compressible bag and an external heat shrink actor material partially arranged around the bag before subjection to heat, FIG. 6 is a schematic cross section of the medicament container of FIG. 5 after subjection to heat, FIG. 7 is a schematic longitudinal section of a medicament container with a rigid core having drain channels, an integrated sensor and an energy store, and FIG. 8 is a schematic lateral section of a subdivided medicament container with a segmented rigid core.

FIG. 9 is a schematic lateral section of one embodiment of the invention illustrating the outlet having an attached needle and a valve.

Corresponding parts are marked with the same reference symbols in all figures.

DETAILED DESCRIPTION

Figure 1:
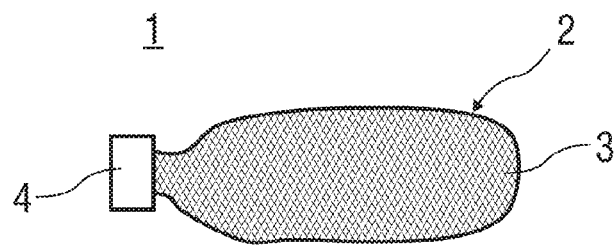
FIG. 1 is a schematic lateral view of a medicament container comprising a bag consisting of a heat shrink material before subjected to heat.

FIG. 1 shows a schematic lateral view of a medicament container 1 comprising a bag 2 consisting of a heat shrink material. The bag stores a liquid medicament 3. One end of the elongate bag 2 has an outlet 4 comprising an interface for attaching a hollow injection needle or an array of Needles. FIG. 9 illustrates one example where needle 21 is attached to outlet 4 that incorporates a valve 20.

Figure 2:
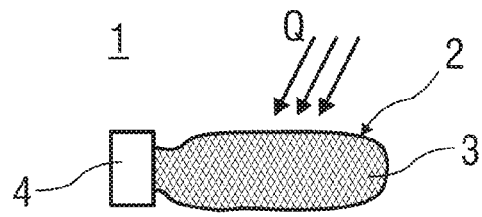
FIG. 2 is a schematic lateral view of the medicament container of FIG. 1 after subjection to heat.

When the bag 2 is subjected to heat Q it is caused to shrink and the liquid medicament 3 stored inside is displaced and thereby delivered through the outlet 4. FIG. 2 shows the medicament container 1 after subjection to heat Q.

Figure 3:
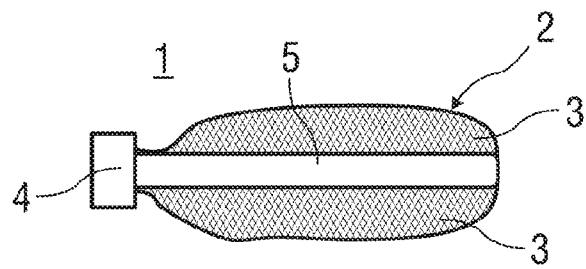
FIG. 3 is a schematic lateral view of an embodiment of the medicament container with a rigid core arranged inside the bag before subjection to heat.

In order to avoid the dead volume shown in FIG. 2 the bag 2 may have a rigid core 5 arranged inside, as shown in FIG. 3.

Figure 4:
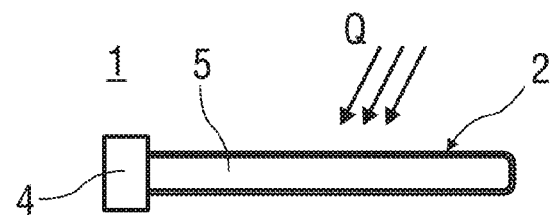
FIG. 4 is a schematic lateral view of the medicament container of FIG. 3 after subjection to heat.

After application of heat Q the bag 2 shrinks and displaces virtually all of the liquid medicament 3, so residual volume is avoided which is particularly important with expensive medicaments. The situation after heating is shown in FIG. 4. Preferably an outline of the rigid core 5 essentially equals an internal diameter of the bag 2 after heating.

FIG. 5 is a schematic cross section of an alternative embodiment of a medicament container 1 with a compressible bag 2 and an external heat shrink actor material 6 partially arranged around the bag 2. FIG. 5 shows the medicament container 1 before being heated. The ends of the actor material 6 are held in fixing points 7 and the actor material 6 is guided over a guide roll 8. When heating a remote section 6.1 of the actor material 6 the actor material 6 shrinks, i.e. shortens and compresses the bag 2, as shown in FIG. 6.

The bag 2 may be arranged to be compressible or shrinkable by subjection of at least a part of the medicament container 1 to an energy source other than heat Q, e.g. radiation or a mechanical impact. The bag 2 may be flexible.

The heat shrink material may be a thermoplastic material such as polyolefin, fluoropolymer (such as FEP, PTFE or Kynar), PVC, neoprene, silicone elastomer or Viton.

The actor material 6 may be alternatively entirely heated.

In a further alternative, the actor material 6 may comprise several sections which may be heated separately (not shown), whereby each section corresponds with a predetermined injection dose.

The embodiment shown in FIGS. 5 and 6 may be combined with the rigid core 5 shown in FIGS. 3 and 4.

The hollow injection needle may be integrated with the medicament container 1.

The medicament container 1 may be part of an injection arrangement or an inhaler arrangement for delivering a liquid medicament to a human or an animal.

The medicament container 1 may also be part of a jet injector having a jet nozzle instead of the needle.

FIG. 7 is a schematic longitudinal section of a medicament container 1 with a rigid core 5 similar to the medicament container 1 of FIG. 3. Additionally, the medicament container 1 of FIG. 7 exhibits drain channels 9 in the rigid core 5. After application of heat Q the bag 2 shrinks and displaces virtually all of the liquid medicament 3. Non-uniform heating or subjection to energy may lead to non-uniform shrinking in such a manner that the shrunk bag seals against the rigid core 5 near the outlet 4 while residual medicament 3 is still trapped in more remote areas. This problem is avoided by the drain channels 9 in the rigid core 5 allowing the bag 2 to shrink until being flush with the rigid core 5 so as to be reliably emptied irrespective of the uniformity of the shrinking process.

The medicament container 1 of FIG. 7 furthermore exhibits a sensor 10 integrated in the rigid core 5. The sensor 10 may serve for determining the state of the liquid medicament 3, e.g. by acquiring a pressure and/or a temperature and/or a pH-value of the medicament.

An energy store 11, such as a battery, may be arranged in the rigid core 5. The energy store 11 may be arranged for powering the sensor and/or for providing the energy required to shrink the bag 2.

An end of the rigid core 5 in FIG. 7 opposite the outlet 4 is arranged as an interface 12 for exchanging data of the sensor 10 and/or energy from the energy store 11 between the medicament container 1 and at least one external component (not illustrated).

FIG. 8 is a schematic lateral section of another embodiment of the medicament container 1. The bag 2 is subdivided into a multitude of bag chambers 2.1 to 2.5. The bag chambers 2.1 to 2.5 may be interconnected for fluid communication as in FIG. 8. Alternatively, the bag chambers 2.1 to 2.5 may be separate from each other. The separate bag chambers 2.1 to 2.5 may contain different medicaments 3. The bag chambers 2.1 to 2.5 may have the same or different volumes. These volumes may be used for fixed doses and/or variable doses.

The rigid core 5 of FIG. 8 is segmented so as to account for the bag 2 being subdivided into bag chambers 2.1 to 2.5. Each segment exhibits an opening of the drain channel 9. Each segment may comprise has a central bulge 5.1.

The rigid core 5 may have a variety of shapes, such as cylindrical, spherical, cuboid, etc.

Preferably, the volume of the rigid core 5 is greater than the remaining volume of the bag 2 after shrinking so as to avoid residual medicament. The remaining volume of the bag 2 after shrinking may be calculated by means of a shrinking factor of the bag material.

The length of the rigid core 5 may differ from the length of the bag 2.

In another embodiment the bag 2 may be subjected to heat or another energy source by means of an annular component arranged for partially surrounding the bag 2. The bag 2 is shrunk by controlled, stepwise or continuous advancement of the annular component, starting from the end opposite the outlet 4 towards the outlet 4. This prevents formation of cavities with residual medicament. Dosage accuracy may be likewise increased.

The embodiment shown in FIGS. 5 and 6 may likewise be combined with the rigid cores 5 shown in FIGS. 7 and 8.

The medicament container 1 may preferably be used for delivering one of an analgetic, an anticoagulant, insulin, insulin derivate, heparin, Lovenox, a vaccine, a growth hormone, a peptide hormone, a protein, antibodies and complex carbohydrates.

The term "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39), des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. A medicament container for a liquid medicament, the medicament container comprising: a bag with an outlet, the bag being compressible or shrinkable by subjection of at least a part of the medicament container to an energy source, characterized in that a rigid core is arranged in the bag, where said bag consists of heat shrink material being configured to shrink when subjected to heat (q).

2. Medicament container according to claim 1, characterized in that the bag is compressible or shrinkable by subjection of at least a part of the medicament container to a heat source.

3. Medicament container according to claim 1, characterized in that an actor material is at least partially arranged around the bag, the actor material being configured to shrink when subjected to heat (Q).

4. Medicament container according to claim 3, characterized in that the actor material comprises several sections which may be heated separately.

5. Medicament container according to claim 3, characterized in that the actor material comprises a remote section, which is not in contact with the bag and which is arranged for being subjected to heat (Q).

6. Medicament container according to claim 1, characterized in that the rigid core is arranged in a longitudinal direction of the bag.

7. Medicament container according to claim 1, characterized in that the outlet comprises an interface for receiving a hollow injection needle.

8. Medicament container according to claim 1, characterized in that at least one drain channel is arranged in the rigid core in a manner to connect at least one opening on a surface of the rigid core to the outlet.

9. Medicament container according to claim 8, characterized in that the bag is subdivided into at least two consecutive bag chambers, wherein the rigid core comprises a respective segment for each bag chamber, each segment having at least one opening of the drain channel.

10. Medicament container according to claim 9, characterized in that each segment comprises a central bulge.

11. Medicament container according to claim 1, characterized in that at least one sensor is integrated in the rigid core.

12. Medicament container according to claim 11, characterized in that an end of the rigid core opposite the outlet is arranged as an interface for exchanging data of the sensor and/or energy from an energy store between the medicament container and at least one external component.

13. Medicament container according to claim 1, characterized in that an energy store is integrated in the rigid core.

14. Injection arrangement for delivering a liquid medicament comprising a medicament container according to claim 1 and a hollow needle for piercing a patient's skin arranged at the outlet.

15. Injection arrangement according to claim 14, characterized in that a valve and a hollow needle for piercing a patient's skin are arranged at the outlet.

16. Inhaler arrangement for delivering a liquid medicament comprising a medicament container according claim 1.

* * * * *